United States Patent
Torre-Bueno

(10) Patent No.: US 6,674,896 B1
(45) Date of Patent: Jan. 6, 2004

(54) DEVICE FOR APPLYING ACCURATE COLOR THRESHOLDS IN REAL TIME

(75) Inventor: Jose De La Torre-Bueno, Encinitas, CA (US)

(73) Assignee: Chromavision Medical Systems, Inc., San Juan Capistrano, CA (US)

( * ) Notice: Subject to any disclaimer, the term of this patent is extended or adjusted under 35 U.S.C. 154(b) by 645 days.

(21) Appl. No.: 09/615,260

(22) Filed: Jul. 13, 2000

Related U.S. Application Data

(60) Provisional application No. 60/143,828, filed on Jul. 13, 1999.

(51) Int. Cl.[7] .................................................. G06K 9/00
(52) U.S. Cl. ........................................ 382/162; 348/587
(58) Field of Search ................................ 382/162–167, 382/279–286; 348/586–603

(56) References Cited

U.S. PATENT DOCUMENTS

| | | | | |
|---|---|---|---|---|
| 4,718,089 A | * | 1/1988 | Hayashi et al. ............. 348/592 |
| 4,991,223 A | | 2/1991 | Bradley ........................ 382/17 |
| 5,087,965 A | | 2/1992 | Torre-Bueno ................ 358/22 |
| 5,233,684 A | | 8/1993 | Ulichney | |
| 5,400,081 A | * | 3/1995 | Chaplin ....................... 348/587 |
| 5,583,666 A | | 12/1996 | Ellson et al. | |
| 5,602,941 A | | 2/1997 | Charles et al. | |
| 5,691,779 A | | 11/1997 | Yamashita et al. | |
| 5,907,315 A | * | 5/1999 | Vlahos et al. ............... 348/586 |
| 5,937,104 A | * | 8/1999 | Henderson et al. ......... 382/279 |
| 6,288,703 B1 | * | 9/2001 | Berman et al. ............. 382/586 |
| 6,301,382 B1 | * | 10/2001 | Smith et al. ................ 382/162 |

FOREIGN PATENT DOCUMENTS

| | | |
|---|---|---|
| JP | 10234079 | 9/1998 |
| KR | 10-0186222 | 12/1998 |

OTHER PUBLICATIONS

Notice of Rejection, Dated: Sep. 3, 2002 in JP Application No. 2001–106997.

\* cited by examiner

*Primary Examiner*—Jingge Wu
(74) *Attorney, Agent, or Firm*—Fish & Richardson P.C.

(57) ABSTRACT

A keyed color generator for use in a machine vision system may include three color channels with a subtractor in each to subtract a corresponding component color of a background on which the object under inspection is being observed. This subtraction operation produces adjusted red (R), green (G), and blue (B) values. The R and B values may be divided by the adjusted G value to produce R/G and B/G color ratios. These color ratios and the adjusted G value may be compared to associated upper and lower threshold values corresponding to a keyed color. If all of the calculated values fall within the associated ranges, the generator outputs a signal indicative of the keyed color.

9 Claims, 3 Drawing Sheets

DEVICE FOR APPLYING ACCURATE COLOR THRESHOLDS IN REAL TIME

CROSS-REFERENCE TO RELATED APPLICATIONS

This application claims priority to U.S. Provisional Patent Application Ser. No. 60/143,828, filed Jul. 13, 1999.

BACKGROUND

Machine vision systems may be used to inspect objects based on their color(s). In industrial applications, such vision systems may inspect the colors of, for example, work pieces, produce, and color-coded pills. Color may be an important indicator of whether a colored component is properly placed in a work piece, whether produce is ripe or overripe, or whether a particular color-coded pill is in the proper location in its container. Such vision systems may also be used in medical applications to determine the composition of cells, in which different cell components are dyed different colors.

Pixels in digital images may have one of thousands, even millions, of possible color values (e.g., 16 bit and 24 bit color). Machine vision systems may be interested in ranges of related color values which fall between upper and lower thresholds. These ranges of color values may be referred to as keyed colors. Transforming a raw pixel color value to a keyed color may simplify downstream processing in the vision system.

In imaging analysis, the observed color of an object may be affected by the background on which it is observed. In such situations, the observed color tends to smear toward the background color. For example, a thin cell component dyed blue and observed on an illuminated slide may appear light blue to an imaging system. For thicker objects, shading or highlights on the object may be affected by the background color. Such background effects may adversely affect the transformation of an observed pixel color value to an appropriate keyed color.

SUMMARY

A keyed color generator according to an embodiment may include several color channels, each corresponding to a color component value, e.g., red, green, and blue components (RGB). The color component values for a scanned pixel are determined and input to the device. These values may be eight bit words.

A corresponding component color value of a background color is subtracted from the pixel component color value in each channel to produce adjusted color values. An adjusted color value may be divided by another color value to produce a color ratio. An adjusted color value and at least one color ratio are compared to associated upper and lower threshold values of a keyed color range. If the adjusted color and color ratios fall within the respective ranges, a signal indicative of a corresponding keyed color may be generated.

For example, in a system utilizing RGB values, R/G and B/G color ratios may be compared to respective upper and lower threshold values and the adjusted G value compared to associated upper and lower threshold values.

The keyed color generator may select between a number of keyed colors, and may operate at a dot clock rate for real time analysis of the image.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
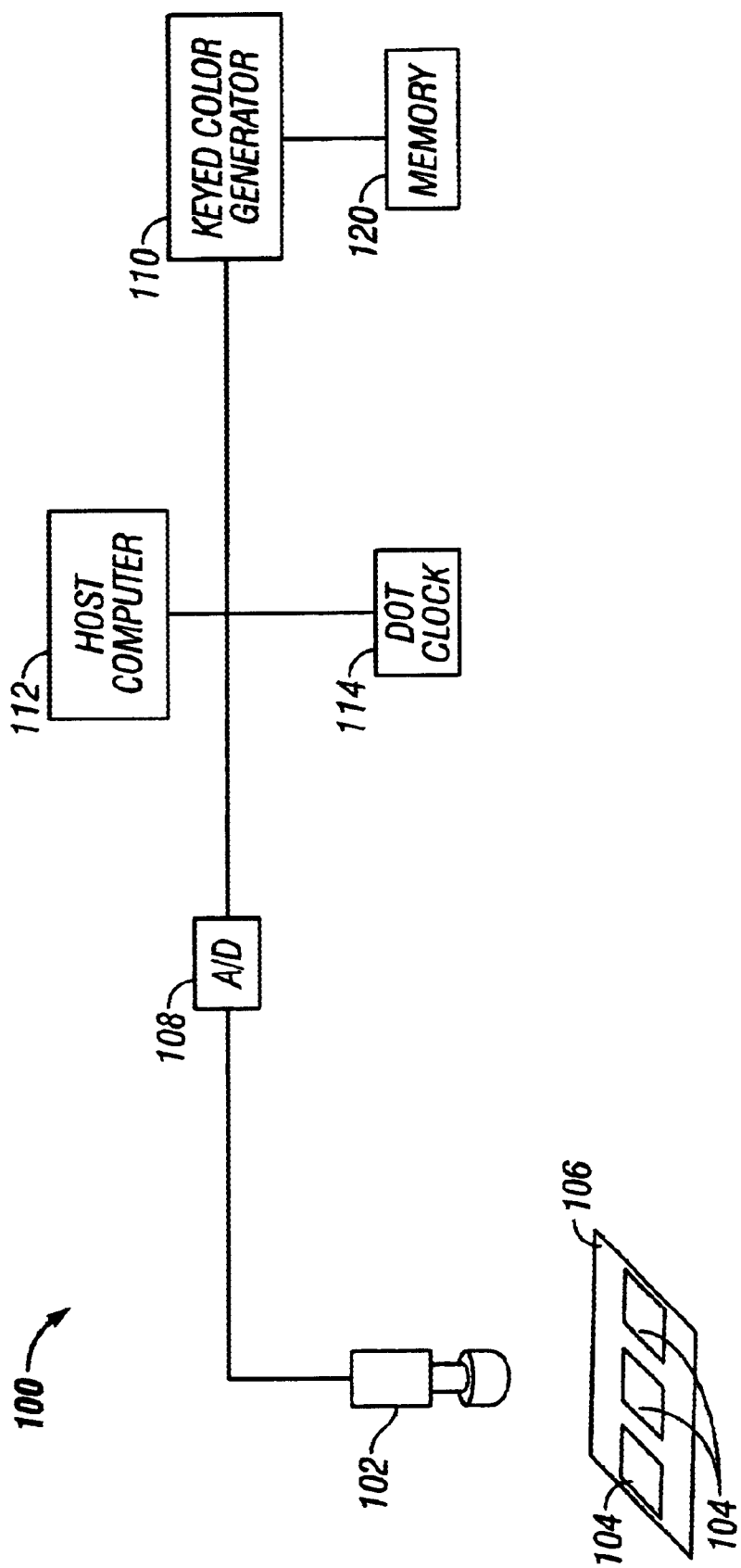
FIG. 1 is a schematic diagram of a machine vision system according to an embodiment.

FIG. 1 illustrates a machine vision system 100 according to an embodiment. A camera 102, which may be analog or digital, scans the images of objects 104 on a background 106. The output of the camera may be digitized (if analog) by an analog-to-digital converter (ADC) 108. The object under inspection may be imaged in a frame of pixels, for example, an array of 680×480 pixels. The camera may output frames at a rate of, for example, 1/60 second.

Each pixel represents the instantaneous value of an optical quality (e.g., color) of the image at a location corresponding to the pixel's position in the frame. A keyed color generator 110 operates on the raw color value of the pixel being scanned and determines if the pixel color value falls within a range of values corresponding to a particular keyed color. If so, the keyed color generator outputs a signal corresponding to that keyed color as the pixel is read out. A host computer 112 reads the keyed color generator output via a device bus with address and data paths 202, 204 (FIG. 2).

Figure 2:
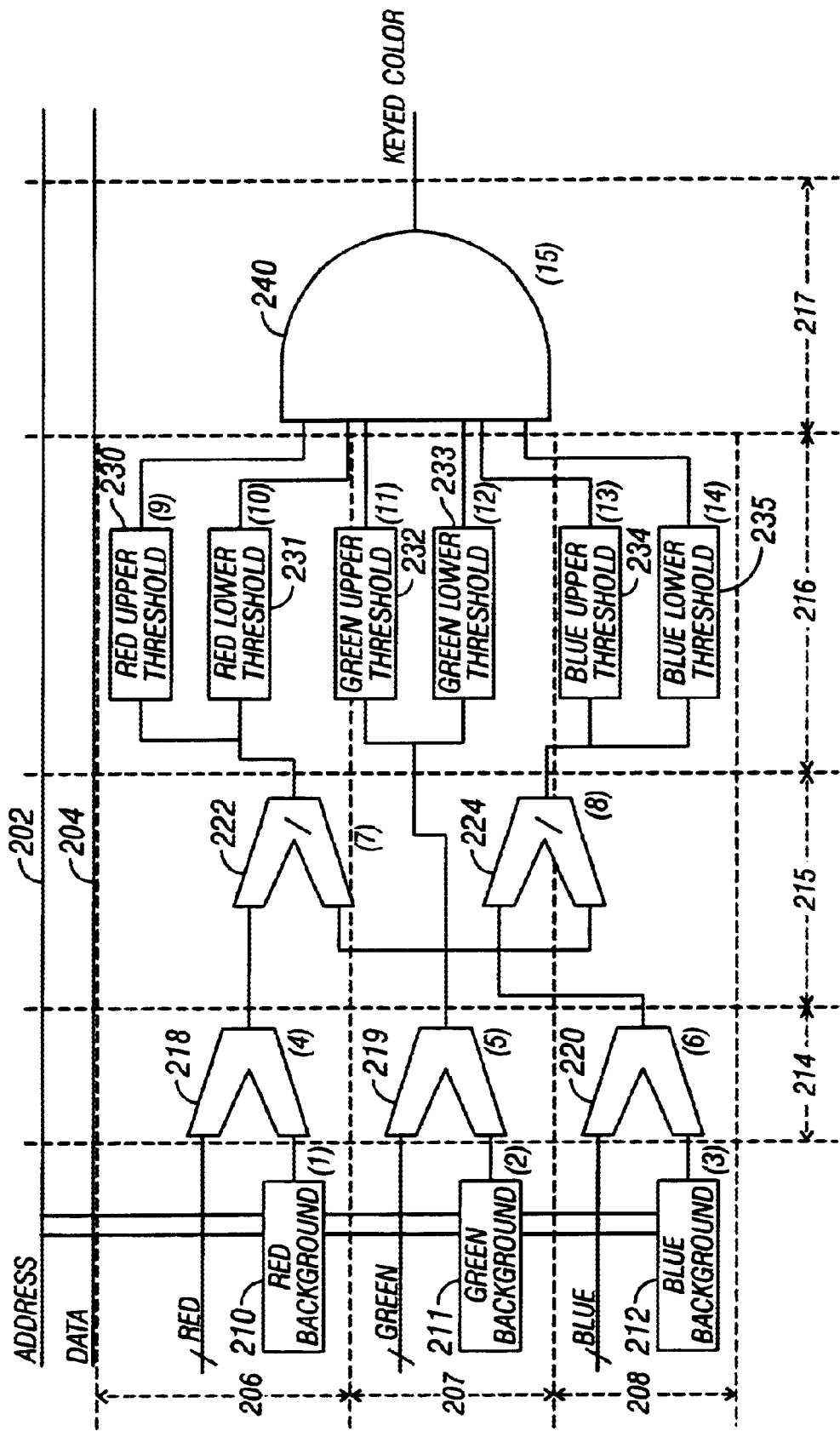
FIG. 2 is a schematic diagram of a keyed color generator according to an embodiment.

According to an embodiment, the video signal may be divided into red, green, and blue (RGB) color components by a digitizer and input to the keyed color generator in three color channels 206–208, one for each color component, as shown in FIG. 2. A dot clock 114 (FIG. 1) generates signals corresponding to the frequency at which pixels are being scanned in the image. The keyed color generator is clocked by the dot clock 114, and hence operates at the dot clock rate. For a camera producing a frame of 680×480 pixels every 1/60 second, this rate may be about 19.6 MHz. At each dot clock signal, the component RGB color values corresponding to the raw color value of a pixel being scanned is input to the keyed color generator. According to an embodiment, the component color values may be eight bit words.

A background value color may be determined before the real time analysis begins by examining a scanned frame of the background. Each of the background color's RGB component values may be stored in a corresponding register 210–212 in each color channel 206–208.

Figure 3:
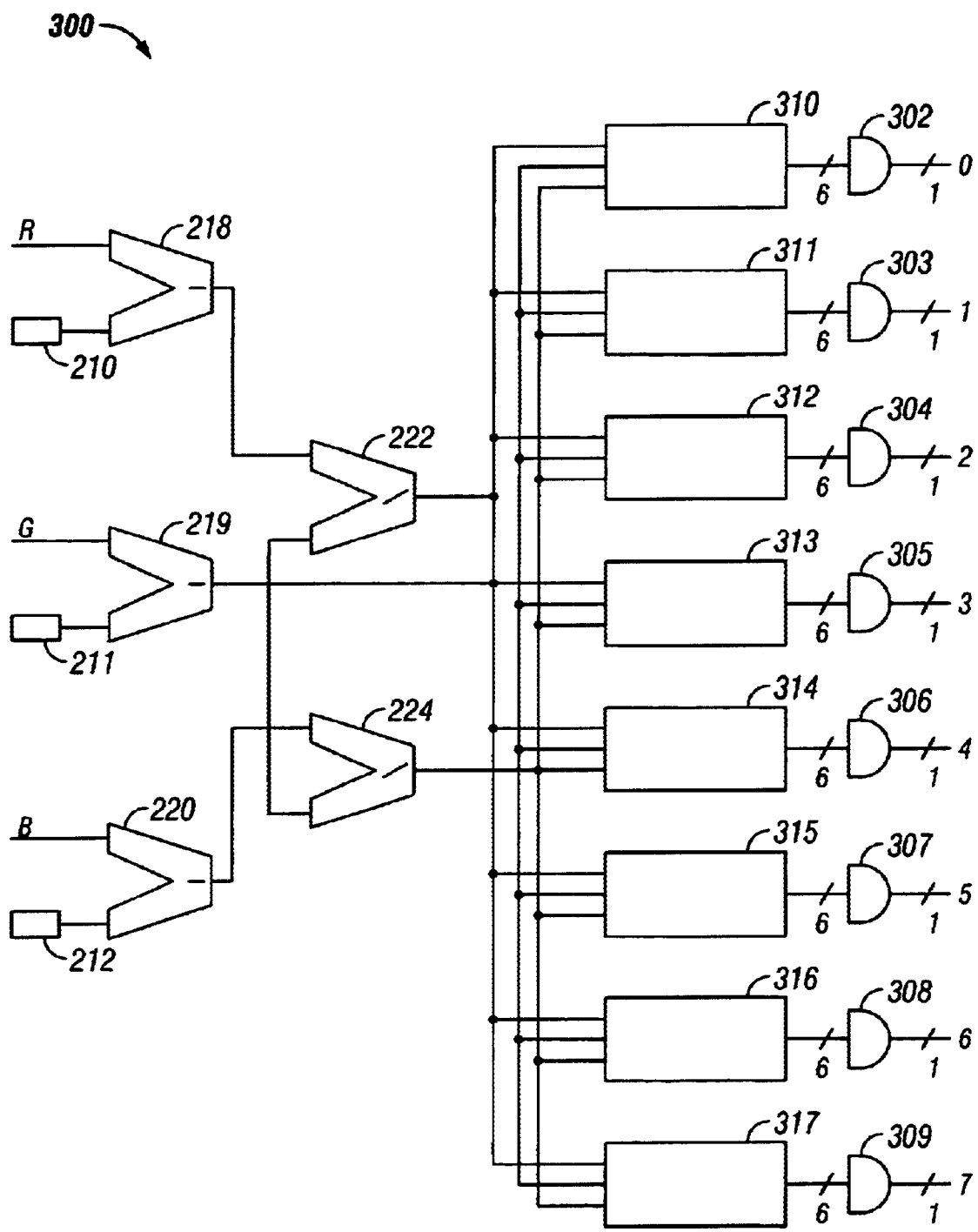
FIG. 3 is a schematic diagram of a keyed color generator according to another embodiment.

The keyed color generator may have several stages 214–217, as shown in FIG. 3, and may operate in a pipelined fashion. In stage 214, a background component color value is subtracted from each component color value of the current pixel by arithmetic logic units (ALUs) 218–220 to produce adjusted color values.

Color values may be conceptualized as existing in color space in which a color value is viewed as a location in a three dimensional coordinate system defined by color axes. According to an embodiment, these axes may be R, G, and B. Subtracting the component background color values from the RGB values of the raw pixel color effectively shifts the center of the coordinate system to a point corresponding to the background color value.

According to an alternate embodiment, the subtraction may be performed in software using a lookup table loaded with adjusted values corresponding to particular input component values.

In stage 215, the adjusted red and blue values are divided by the adjusted green value by divisors 222 and 224 to produce R/G and B/G color ratios. Unlike the adjusted green value, these color ratios do not depend on the brightness of the object. This division stage effectively transforms the RGB coordinate system to a new coordinate system. This coordinate system includes one axis corresponding to brightness (green) and two axes representing color elements independent of brightness (R/G and B/G).

In stage 216, each of the R/G and B/G color ratios and the adjusted green value are input to a corresponding pair of register/comparators. Each register/comparator pair includes an upper threshold register/comparator 230, 232, 234 and a lower threshold register/comparator 231, 233, 235. At setup, the host computer 112 may load each upper threshold register/comparator with a digital value corresponding to an upper value in the range of values corresponding to a keyed color, and may load each lower threshold register/comparator with a digital value corresponding to a lower value in the keyed color range. These upper and lower threshold values on each axis define a three-dimensional space in the coordinate system including a range of values corresponding to a particular keyed color.

The R/B and B/G color ratios and adjusted green values are compared to the corresponding upper and lower threshold values in the register/comparators. If the input value is below the value stored in the upper threshold value, the upper threshold register/comparators will output a "1", and if the input value is higher than the upper threshold value, output a "0". If the input value is above the value stored in the lower threshold value, the lower threshold register/comparators will output a "1", and if the input value is lower than the lower threshold value, output a "0".

In stage 217, the 1 bit values output from the register/comparators are combined in a six-input AND gate 240. If all of the register/comparators output a "1", the AND gate will output a HIGH value and the device will output a value corresponding to the keyed color associated with those thresholds. If any register/comparator outputs a "0" value, the raw color value of the pixel is considered outside the range of colors corresponding to the keyed color and the AND gate will output a LOW value for that pixel.

According to various embodiments, the function of each of stages 214–217 may be implemented in hardware, software, or various combinations of both.

FIG. 3 illustrates an embodiment in which the keyed color generator 300 analyzes the input color value to determine if it corresponds to any of eight keyed colors. The circuitry in stages 216 and 217 (FIG. 2) are replicated for each keyed color such that each one of eight AND gates 302–309 is connected to an associated bank 310–317 of six registers. The outputs of the eight AND gates 302–309 may be input to an encoder which outputs a three bit number identifying the keyed color associated with the each AND gate.

The pixel color value may be tested against several thresholds simultaneously. According to an embodiment, the thresholds for the keyed colors may be set such that they do not overlap. Thus, only one keyed color may be output for each scanned pixel.

According to another embodiment, a pixel color value may fall into more than one range, causing more than one AND gate to output a HIGH value for a given pixel. According to an embodiment, a pixel may be associated with more than one keyed color. The output of each AND gate that goes HIGH is preserved for processing downstream. According to an alternate embodiment, only one keyed color may be associated with a pixel. This keyed color may be determined by a set of rules stored in a memory 120 (FIG. 1) connected to the keyed color generator. The rules may give priority to one keyed color over other keyed colors. Alternatively, a keyed color may be associated with a particular pixel color value in a lookup table. If more than one AND gate goes HIGH for a given pixel, the keyed color generator may access the lookup table to determine the appropriate keyed color for that pixel color value.

According to alternate embodiments, the system may operate on more or less than eight bit color values. According to these embodiments, the ALUs, registers, and comparators have a depth large enough to accommodate the size of the color values.

A machine vision system according to an embodiment may be used for a variety of industrial and medical applications including, for example, inspecting colored components in a work piece, produce, color-coded pills, textiles, and stained cells.

A number of embodiments of the invention have been described. Nevertheless, it will be understood that various modifications may be made without departing from the spirit and scope of the invention. Accordingly, other embodiments are within the scope of the following claims.

What is claimed is:

1. An apparatus comprising:
    a plurality of color channels, each color channel corresponding to a different component color value, and comprising a subtractor to subtract a component color value of a background color from a component value of a pixel color to produce an adjusted color value;
    a divider to divide at least one of said component color values by another of said component color values to produce a color ratio;
    a keyed color indicator to generate a signal in response to each of the adjusted color value and the color ratio falling within an associated range of values corresponding to a keyed color;
    a first subtractor in a first color channel to subtract a first color component of a background color from a first color component of an input pixel color to produce a first adjusted value;
    a second subtractor in a second color channel to subtract a second color component of the background color from a second color component of the input pixel color to produce a second adjusted value;
    a divider to divide the first adjusted value by the second adjusted value to produce a first color ratio;
    a first comparison circuit to determine if the first color ratio falls in a first range of values;
    a second comparison circuit to determine if the second adjusted color falls in a second range of values; and
    a logic circuit to output a signal indicative of a keyed color in response to the first color ratio falling within the first range and the second adjusted color falling within the second range.

2. The apparatus of claim 1 further comprising a third subtractor in a third color channel to subtract a third color component of the background color from a third color component of the input pixel color to produce a third adjusted value;
    a second divider to divide the third adjusted value by the second adjusted value to produce a second color ratio;
    a third comparison circuit to determine if the second color ratio falls in a third range of values, and wherein the logic circuit outputs a signal indicative of a keyed color in response to the first color ratio falling within the first range and the second adjusted color falling within the second range and the second adjusted color ratio falling within the third range of values.

3. The apparatus of claim 2, wherein the first color component comprises red, the second color component comprises green, and the third color component comprises blue.

4. The apparatus of claim 1, wherein said first and second comparison circuits and the logic circuit comprise a stage, and wherein said stage is replicated for each of a plurality of keyed colors, and wherein said comparison circuits in each stage comprise a different range of values.

5. The apparatus of claim 1, wherein the first comparison circuit comprises a first comparator to compare the first color ratio to an upper threshold value and a second comparator to compare the first color ratio to a lower threshold value, and wherein the second comparison circuit comprises a third comparator to compare the second adjusted color to an upper threshold value and a fourth comparator to compare the second adjusted color to a lower threshold value.

6. The apparatus of claim 1, wherein each of the color component values comprises an eight bit words.

7. The apparatus of claim 1, wherein the keyed color indicator operates at a dot clock rate.

8. A system comprising:

a camera to image an object;

a digitizer connected to the camera to digitize the image into a frame comprising a plurality of pixels, each pixel having a color value; and a keyed color generator comprising:

a plurality of color channels, each color channel corresponding to a different component color value, and comprising a subtractor to subtract a component color value of a background color from a component value of a pixel color to produce an adjusted color value;

a divider to divide at least one of said component color values by another of said component color values to produce a color ratio;

a keyed color indicator to generate a signal in response to each of the adjusted color value and the color ratio falling within an associated predetermined range of values;

a first subtractor in a first color channel to subtract a first color component of a background color from a first color component of an input pixel color to produce a first adjusted value;

a second subtractor in a second color channel to subtract a second color component of the background color from a second color component of the input pixel color to produce a second adjusted value;

a third subtractor in a third color channel to subtract a third color component of the background color from a third color component of the input pixel color to produce a third adjusted value;

a first divider to divide the first adjusted value by the second adjusted value to produce a first color ratio;

a second divider to divide the third adjusted value by the second adjusted value to produce a second color ratio;

a first comparison circuit to determine if the first color ratio falls in a first range of values;

a second comparison circuit to determine if the second adjusted color falls in a second range of values;

a third comparison circuit to determine if the second color ratio falls in a third range of values; and a logic circuit to output a signal indicative of a keyed color in response to the first color ratio falling within the first range and the second adjusted color falling within the second range and the second color ratio falling with the third range of values.

9. The system of claim 8, wherein the keyed color indicator operates at a dot clock rate.

* * * * *